(12) United States Patent
Zucca et al.

(10) Patent No.: US 7,863,023 B2
(45) Date of Patent: Jan. 4, 2011

(54) STEREOSELECTIVE PREPARATION OF GAMMA-LACTONES

(75) Inventors: Joseph Zucca, Grasse (FR); Jean Mane, Grasse (FR)

(73) Assignee: V. Mane Fils, Bar-sur-Loup (FR)

( * ) Notice: Subject to any disclaimer, the term of this patent is extended or adjusted under 35 U.S.C. 154(b) by 795 days.

(21) Appl. No.: 11/666,734

(22) PCT Filed: Nov. 2, 2005

(86) PCT No.: PCT/FR2005/002730

§ 371 (c)(1),
(2), (4) Date: May 31, 2007

(87) PCT Pub. No.: WO2006/048551

PCT Pub. Date: May 11, 2006

(65) Prior Publication Data

US 2008/0108116 A1    May 8, 2008

(30) Foreign Application Priority Data

Nov. 3, 2004   (FR)  .................................. 04 11722

(51) Int. Cl.
*C12P 17/04*    (2006.01)
(52) U.S. Cl. .................... 435/126; 435/171; 435/254.1; 435/256.1

(58) Field of Classification Search ................. 435/126, 435/171, 254, 4, 256.1
See application file for complete search history.

(56) References Cited

U.S. PATENT DOCUMENTS

| | | | |
|---|---|---|---|
| 4,560,656 A | 12/1985 | Farbood et al. | |
| 4,950,607 A | 8/1990 | Cardillo et al. | |
| 5,166,366 A | 11/1992 | Farbood et al. | |
| 5,457,036 A | 10/1995 | Han et al. | |

FOREIGN PATENT DOCUMENTS

| | | |
|---|---|---|
| DE | 41 26 997 | 2/1993 |
| EP | 0 258 993 | 3/1988 |
| EP | 0 519 481 | 12/1992 |

*Primary Examiner*—Sandra Saucier
*Assistant Examiner*—Susan Hanley
(74) *Attorney, Agent, or Firm*—Young & Thompson

(57) ABSTRACT

Method for stereoselectively preparing a (R) or (S) gamma-lactone consists in microbially biosynthesizing gamma-lactone, wherein the biosynthesis is carried out from a substrate selected from C5 to C20 fatty acids with the aid of a strain selected from those enabling a stereoselective hydroxylation in C4 of the substrate, in particular *Aspergollus* sp or *Mortierella* sp. The biosynthesis of the gamma-lactone and the use thereof in perfumery and for food flavouring agents are also disclosed.

13 Claims, No Drawings

STEREOSELECTIVE PREPARATION OF GAMMA-LACTONES

This application is a national stage entry of PCT/FR05/02730, filed Nov. 2, 2005, which claims priority to French application number 0411722, filed Nov. 3, 2004.

The present invention relates to a process for the stereoselective synthesis of gamma-lactones, in particular of natural gamma-lactones.

"Natural" products are increasingly appreciated by the general public and, as a result, industries that use aromatic or odorant compounds concentrate their efforts on the development of "natural" aromatizing substances and preparations. Only substances that have been identified in nature can aspire to this label; they are therefore currently produced either from plants or from microorganisms; the latter are increasingly used, biotechnological processes now making it possible to synthesize natural molecules at reasonable expense. This is the case of gamma-lactones.

Gamma-lactones are aromatic molecules that constitute the aroma and the flavor of many natural products. For example, gamma-heptalactone is known for its hazelnut or caramel aroma and taste, gamma-nonalactone has a fatty, creamy, or coconut aroma; gamma-decalactone and gamma-undecalactone have a peach or apricot aroma and taste.

Gamma-lactones exist naturally, in their two enantiomeric forms (R) and (S), the (R) enantiomer being, however, predominant.

Gamma-lactones can be produced synthetically, or by biosynthesis by means of microorganisms. Thus, EP 371 568 describes a process for producing gamma-lactones by means of microorganisms that are acceptable for preparing food products, such as *Saccharomyces cerevisiae, Debaromyces hansenii* or *Candida boidinii*.

U.S. Pat. No. 5,112,803 indicates that gamma-octalactone, and in particular its (R) and (S) optical isomers, can be used to form butter aromas and flavors, and describes a process for increasing the aroma or the flavor of materials that can be consumed, by adding significant amounts of optically active gamma-octalactones, and a mixture of various compounds which are by-products of the biological process described. The process described in U.S. Pat. No. 5,112,803 indicates that, using caprylic acid, it is possible to obtain the two (R) and (S) isomers of gamma-octalactone by biosynthesis using strains of the genus *Syncephalastratum* sp or *Mortierella* sp.; however, this process is not enantioselective.

Gamma-lactones are of great value in the food flavoring industry and in the perfumery industry, and real industrial high stakes are involved in the production of products that have different organoleptic nuances.

It is known that the chirality of volatile molecules can induce differences in terms of olfactory perception, and that the optical isomers of gamma-lactones do not all have the same organoleptic notes: there is therefore a considerable advantage in producing a specific optical isomer of gamma-lactone, in particular if this production is carried out according to a process that is at least as efficient, or even more efficient, than in the prior art and at a competitive cost.

To date, to the applicant's knowledge, no stereo-selective process exists for directly obtaining an enantiomer of natural gamma-lactones. The known processes produce mixtures of enantiomers, the separation of the desired enantiomer generally being carried out by gas chromatography on a capillary column of substituted cyclodextrin, or after derivatization.

An object of the invention is therefore to propose a process for the biological synthesis of a gamma-lactone that is efficient, economical and stereoselective.

The invention relates to both the synthesis of (R)-gamma-lactones and of (S)-gamma-lactones. For the purpose of the present invention, (R) and (S) denote the position of the asymmetric carbon in position 4 of the gamma-lactone.

The gamma-lactones that are preferred for synthesis according to the process of the invention are the $C_5$-$C_{20}$ gamma-lactones in accordance with the invention corresponding to formula (I):

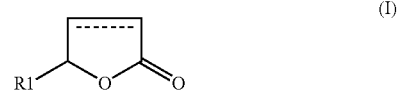

in which the lactone ring can bear an unsaturation between carbon no. 2 and carbon no. 3, and in which R1 is a $C_{1-16}$ alkenyl, $C_{1-16}$ alkynyl or $C_{1-16}$ alkyl group, optionally having one or more substituted carbons beyond position no. 5. The expression "substituted alkenyl or alkynyl or alkyl" is intended to mean an alkenyl or alkynyl or alkyl in which at least one carbon bears at least one substituent group. The term "substituent group" is intended in particular to mean a hydroxyl group, a keto group, a thiol group, an alkyl group or an alkenyl group.

The invention therefore relates to a process for the stereoselective preparation of a gamma-lactone, characterized in that a microbial biosynthesis of a gamma-lactone is carried out, in particular of a gamma-lactone of general formula (I) above, in which the lactone ring can bear an unsaturation between carbon no. 2 and carbon no. 3, and is preferably saturated, and in which R1 is an optionally substituted $C_{1-16}$ alkenyl, $C_{1-16}$ alkynyl or $C_{1-16}$ alkyl, said biosynthesis being carried out from at least one substrate, preferably a fatty acid, using a microbial culture of a strain chosen from those that allow stereoselective hydroxylation of said substrate at C4.

The invention relates to the biological preparation of gamma-lactones, and in particular the stereoselective biosynthesis of each of the (R) or (S) optical isomers of gamma-lactones, from at least one substrate, using a microbial culture of an appropriate strain.

This preparation comprises the following steps:
a) selecting an appropriate strain,
b) culturing said strain in an appropriate culture medium, said culturing being optionally preceded by a step consisting in preculturing the strain,
c) adding a substrate that can be converted into gamma-lactone,
d) bioconverting the substrate into gamma-lactone,
e) recovering the gamma-lactone produced.

The appropriate microbial strains, targeted in step a) for the biosynthesis of the gamma-lactone according to the invention, are those that allow specific hydroxylation of the substrate. According to a preferred embodiment of the invention, the appropriate microbial strains, targeted in step a) for the biosynthesis of the gamma-lactone according to the invention, are those that allow specific stereoselective hydroxylation of the substrate at C4. Thus, in accordance with the invention, gamma-lactones in which the carbon C4 is in the (R) configuration or in the (S) configuration, are obtained.

When the product resulting from the biosynthesis is for use in the food industry, the food-grade strains will of course be preferred. Among these strains that allow stereoselective hydroxylation, mention may in particular be made of the strains of the genus *Aspergillus* sp., *Penicillium* sp., *Mucor* sp., and *Mortierella* sp. These strains all belong to microorganism class 1, and since some are food strains, their use does not pose any specific problem neither for the industrial production of lactones or for its possible use in food products. According to a specific embodiment of the invention, the strain used is of the genus *Aspergillus* sp., preferably *Aspergillus oryzae*, of which mention may be made of the following collections of strains:

*Aspergillus oryzae* DSMZ 1861, *Aspergillus oryzae* DSMZ 1864, *Aspergillus oryzae* DSMZ 1147, *Aspergillus oryzae* DSMZ 63303, *Aspergillus oryzae* CBS 570.65, *Aspergillus oryzae* CBS 819.72, *Aspergillus oryzae* CBS 110.27, *Aspergillus oryzae* VMF 88093.

Among them, *Aspergillus oryzae* DSMZ 1861 and *Aspergillus oryzae* CBS 110.27 are preferred.

According to another specific embodiment, the strain used is of the genus *Mortierella* sp., of which mention may be made of the following collections of species: *Mortierella isabellina* DSMZ 1414, *Mortierella isabellina* CBS 100559, *Mortierella isabellina* CBS 221.29, *Mortierella isabellina* CBS 194.28, *Mortierella isabellina* CBS 208.32, *Mortierella isabellina* CBS 224.35, *Mortierella isabellina* CBS 560.63, *Mortierella isabellina* CBS 167.80, *Mortierella isabellina* CBS 493.83, *Mortierella isabellina* CBS 309.93, *Mortierella isabellina* CBS 250.95, *Mortierella isabellina* CBS 109075, *Mortierella ramanniana* CBS 112.08, *Mortierella ramanniana* CBS 219.47, *Mortierella ramanniana* CBS 243.58, *Mortierella ramanniana* CBS 478.63, *Mortierella ramanniana* CBS 852.73, *Mortierella ramanniana* CBS 366.95, *Mortierella ramanniana* CBS 101226.

In fact, the inventors have noted that, surprisingly and unexpectedly, the use of a strain of the genus *Aspergillus* sp. results in the selective production of (R) gamma-lactone, and that the use of a strain of the genus *Mortierella* sp. results in the selective production of (S) gamma-lactone.

According to one embodiment of the invention, *Yarrowia lipolytica* strains are excluded from the invention since they are not capable of bringing about hydroxylation at C4. Advantageously, all strains which are not capable of specifically and selectively producing hydroxylation at C4 are excluded from the present invention.

Without wishing to be bound by any theory, it can be envisioned that the conditions for culturing the strains could be of importance in the stereoselectivity observed, and also in the quantitative aspect of the bioconversion.

The culturing targeted in step b) of the process according to the present invention comprises the preparation of a culture, preferably a semi-concentrated culture, of strains, for example by cell amplification, in an appropriate culture medium. This culturing may be preceded by a preculturing of the strains in a first culture medium more suitable for the first steps of multiplication of the strain.

The culture conditions used in the stereoselective process of the invention should be such that they result in the production of a mycelium which exhibits swellings filled with inclusions (with peroxysomes in particular). According to the preferred embodiment of the invention, the cell culture prepared has a "compot" mycelium composed of compartmentalized filaments with no conidiospores and exhibiting bulging structures, filled with these inclusions (in particular peroxysomes). The culture conditions should in fact be particularly appropriate for preventing sporulation of the mycelium. Moreover, the inventors have been able to note that the physiological state of the mycelium, obtained in particular due to the use of the culture conditions described in the present application (compartmentalized mycelium comprising swellings and bulges filled with inclusions, in particular with peroxysomes), could have a considerable influence on the reaction yield and would make it possible to obtain yields greater than those of the prior art. The physiological state of the mycelium could also have an influence on the stereoselectivity of the reaction.

Thus, according to a preferred embodiment of the invention, step b) of the process of the invention is a step consisting in culturing the strain in an appropriate culture medium for obtaining a compartmentalized mycelium comprising swellings and bulges filled with inclusions, in particular with peroxysomes. Advantageously, the culture medium used according to the invention does not contain peptone. Preferably, the culture medium used according to the invention comprises malt and/or yeast extract. According to a preferred embodiment, the mycelium used for step c) is concentrated. Preferably, the concentration of the mycelium used for step c) is between 5 and 15 g/l, preferably 6 to 12 g/l, very preferably 7 to 10 g/l.

It has been particularly noted that the production of (S)-gamma-lactone by the *Mortierella* strain is particularly promoted, in terms of stereoselectivity and in terms of yield, by the use of a swollen mycelium filled with inclusions as described above; in fact, the use of such a mycelium would make it possible to obtain a reaction product which has an optical rotation greater, in absolute value, than those of the prior art; furthermore, the yield obtained by means of the process according to the invention, and in particular by the use of a swollen mycelium filled with inclusions as described above, makes it possible to obtain yields greater than those of the prior art.

Step c) of the process consists in adding the substrate to the cell culture. According to the invention, the biological synthesis of gamma-lactone involves an appropriate substrate.

For the purpose of the present invention, the term "appropriate substrate" is intended to mean saturated or unsaturated, linear fatty acids containing at least 5 carbons, and preferably from 5 to 20 carbons, optionally branched or substituted beyond position no. 5, and the esters of said fatty acids; methyl or ethyl esters are preferred.

Among the preferred substrates, mention may be made of: valeric acid, which is a $C_5$ acid that produces a gamma-valerolactone; caproic acid, which is a $C_6$ acid that produces a gamma-hexylactone; enanthic acid, which is a $C_7$ acid that produces a gamma-heptalactone; caprylic acid, which is a $C_8$ acid that produces a gamma-octalactone; pelargonic acid, which is a $C_9$ acid that produces a gamma-nonalactone; decanoic acid, which is a $C_{10}$ acid that produces a gamma-decalactone, undecanoic acid, which is a $C_{11}$ acid that produces a gamma-undecalactone; undecylenic acid, which is a $C_{11}$ acid that produces gamma-undecenolactone; lauric acid, which is a $C_{12}$ acid that produces a gamma-dodecalactone; myristic acid, which is a $C_{14}$ acid that produces a gamma-tetradecalactone; palmitic acid, which is a $C_{16}$ acid that produces a gamma-hexadecalactone; palmitoleic acid, which is an unsaturated $C_{16}$ acid that produces a gamma-hexadecenolactone; stearic acid, which is a $C_{18}$ acid that produces a gamma-octadecalactone; oleic acid, which is a $C_{18}$ acid that produces a gamma-octadecenolactone; linoleic acid, which is a $C_{18}$ acid that produces a gamma-octadecadienolactone; linolenic acid, which is a $C_{18}$ acid that produces a gamma-octadecatrienolactone; and eicosanoic acid, which is a $C_{20}$ acid that produces a gamma-eicosanolactone, and esters thereof, preferably ethyl or methyl esters thereof.

Although they are rare, $C_{13}$, $C_{15}$, $C_{17}$ and $C_{19}$ fatty acids, and ethyl or methyl esters thereof, can also be oxidized and produce, respectively, $C_{13}$, $C_{15}$, $C_{17}$ and $C_{19}$ gamma-lactones.

It goes without saying that the substrate can be any appropriate substrate, or a mixture of various appropriate substrates, in particular a mixture of a given acid and of one or more of its esters.

According to an advantageous embodiment of the invention, the substrate is added to the mycelium according to a batchwise or fed-batch process. According to a preferred embodiment, the substrate is added as a mixture with an auxiliary product, for example an oil, in particular any conventional food oil, such as soybean, maize, sunflower, or the like, or synthetic short-chain fatty acid triglycerides such as miglyol, preferably sunflower oil which is hydrogenated or rich in oleic acid, prior to it being brought into contact with the mycelium. The presence of the auxiliary product makes it possible in particular to greatly decrease the corrosive or toxic effect of the substrate. According to one embodiment of the invention, the synthesis according to the invention using the *Mortierella isabellina* strain is carried out in a medium free of mineral oil. Advantageously, the substrate is added in concentrations of from 0.3 to 2.5 g/l/h. Advantageously, the amount of oil, preferably of plant oil, mixed with the substrate is from 100 to 500 g/l, preferably 150 to 300 g/l.

A source of sugar, preferably of glucose, is also added to the medium, at the same time as the substrate, so as to ensure that the energy needs of the cells are covered. Advantageously, the concentration of glucose added is from 0.3 to 0.4 g/l/h.

The pH can be regulated, as needed, during the addition of the substrate and throughout the duration of the bioconversion that will follow, by means of the addition of any appropriate base. Advantageously, the pH is between 4.5 and 8.5, preferably between 5.5 and 8, and preferably between 6 and 7.5.

The temperature is preferably maintained between 27 and 30° C., during the bioconversion. The duration of the bioconversion may be from 30 to 120 hours, preferably from 48 to 72 hours.

The bioconversion of the substrate to gamma-lactone, covered in step d) of the process of the invention, is a step consisting of lactonization preceded by a reaction consisting of hydroxylation of the substrate at C4, carried out by the strain. A source of oxygen is required in order for it to be possible for this hydroxylation to be carried out. This source of oxygen is preferably a gas containing oxygen, very preferably air or oxygen. The gas is dissolved in a relatively large amount in the reaction medium.

According to a preferred embodiment, and as is known in the prior art, antifoams, in particular silicone oils or polymers of polyethylene glycol esterified with fatty acids, are used to control the foam that may form during the bioconversion.

Once the bioconversion, i.e. the specific and stereo-selective hydroxylation at C4, followed by the lactonization, has been carried out, step e) of the process consists in recovering the gamma-lactone by extraction, the extraction of the gamma-lactone being carried out by any appropriate means. Advantageously, the extraction of the gamma-lactone is carried out by hydrodistillation, optionally followed by an esterification intended to subsequently eliminate the substrate which has not reacted.

Alternatively, the extraction of the gamma-lactone is carried out by solvent extraction after acidification of the medium.

According to a variant of the invention, step e) of the process is not carried out, and instead, a step e') is carried out, which step consists in continuing the process at the end of step d) by means of an in situ reduction of the gamma-lactone obtained, before extraction. Step e') makes it possible to obtain an (R)- or (S)-gamma-lactone that is more saturated, depending on the stereochemistry of the gamma-lactone obtained in step d).

According to a first embodiment, the reduction can be carried out until a saturated lactone is obtained. According to a second embodiment, the reduction can be stopped so as to obtain a gamma-lactone whose side chain bears fewer unsaturations than that derived from the bioconversion of step d). According to this other embodiment, the process according to the invention is continued at the end of step d), while stopping the pH regulation of the fermentor, and adding an active dry yeast, which may be a baker's yeast, a wine-maker's yeast or a brewer's yeast, and a source of sugar, in particular of glucose, to the reactor. When the pH reaches the value of 5.5, it is regulated at 5.5 with an appropriate base, for example sodium hydroxide NaOH. The mixture is left to incubate, preferably for a period of 12 to 24 hours, and then the gamma-lactone is extracted. According to another variant, the gamma-lactone derived from step d) can be reduced by means of a fresh culture of a reducing microorganism or a microorganism that is at least placed under reducing conditions, for example *Saccharomyces cerevisiae, Pichia etchelsii, Pichia pastoris, Hansenula polymorpha, Bacillus subtilis* or *Lactobacillus brevis*.

The reduction of step e') results in the production of gamma-lactones that are more saturated than those derived from step d). These more saturated gamma-lactones, obtained according to this specific embodiment, have an asymmetric carbon in position 4 which has the same configuration as that of the less saturated gamma-lactone from which it derives, since the reduction reaction does not modify the stereoisomerism of the molecule.

The gamma-lactones obtained according to the process of the invention have odorant and gustative properties such that they can be used in all perfumery and food flavoring applications, in particular for the production of perfumes, of odorant substances, or of cosmetic or food compositions, or as a food additive.

For the purpose of the present invention, the term "perfumery" denotes not only perfumery in the usual sense of the term, but also the other fields in which the odor of products is important. This may involve perfumery compositions in the usual sense of the term, such as fragrancing bases and concentrates, eaux de cologne, eaux de toilette, perfumes and similar products; topical compositions—in particular cosmetic compositions—such as face and body creams, talcum powders, hair oils, shampoos, hair lotions, bath salts and oils, shower and bath gels, toilet soaps, body antiperspirants and deodorants, shaving lotions and creams, soaps, creams, tooth paste, mouth washes, ointments, and similar products; and maintenance products, such as softeners, detergents, washing powders, air fresheners, and similar products.

The term "odorant" is used to denote a compound which gives off an odor.

The term "food flavoring" is intended to mean any use of the compounds of the invention for the flavoring of any human or animal, liquid or solid food product, in particular drinks, dairy products, ice creams.

The gamma-lactones, (R) or (S), or a mixture of (R) and (S) can be used in perfuming compositions in order to contribute to providing exotic, floral or fruity notes. According to the applications, the (S) enantiomer or the (R) enantiomer, or else a mixture of the 2 enantiomers in proportions determined by a person skilled in the art, will be used.

Preferably, the gamma-lactones obtained by the process of the invention, according to the invention, are used in amounts of between 0.0025% and 10% by weight relative to the total weight of the composition in which they are present. They may go to make up the composition of solids or of liquids, and in particular the composition of gels, creams, ointments and/or sprays.

The gamma-lactones obtained by means of the process of the invention, according to the invention, can also be used in a composition that is itself odorant, or in a composition in which the odorant agent is used to mask or neutralize certain odors.

Other characteristics and advantages of the present invention will emerge clearly upon reading the examples given hereinafter, which illustrate the invention without, however, limiting it.

EXAMPLE 1

Step a: —Selection of Strains

All the strains of the collection are first inoculated onto MGY agar medium and incubated for 72 hours at 27° C.; these strains are subsequently inoculated into 1-liter Erlenmeyer flasks containing 100 ml of 1× malt medium and incubated for 24 h at 27° C. The substrate, undecylenic acid, is then added to the culture medium (5 g/l in 10 doses) and the culture is maintained for a further 48 h to 120 h at 27° C.

After olfaction and analyses of the gamma-undecenolactone concentration in the media, the most advantageous strains are selected; this was the case for the *Mortierella isabellina* CBS 100559, *Mortierella isabellina* CBS 221.29, *Aspergillus oryzae* DSMZ 1861 and *Aspergillus oryzae* CBS 110.27 strains, which were subsequently used for the fermentor optimization trials.

EXAMPLE 1

Step b: —Preparation of Cell Cultures

The *Mortierella isabellina* CBS 100559, *Mortierella isabellina* CBS 221.29, *Aspergillus oryzae* DSMZ 1861 or *Aspergillus oryzae* CBS 110.27 strain (origin=frozen tube at −80° C.) is inoculated on MGY agar and incubated at 27° C. for 30 hours.

The above preculture is inoculated into 5 l of 1× malt medium in a 6 l fermentor:

| | |
|---|---|
| Malt extract: | 165 g |
| Yeast extract: | 25 g |
| H₂O qs: | 5 l |
| pH | 6.5 |

*Mortierella isabellina*

Incubation is carried out at 27° C., 500 rpm, 3.5 l/l/h of air, open pH, for 30 hours.

*Aspergillus oryzae*

Incubation is carried out at 20° C., 500 rpm, 0.05 vvm of air, open pH, for 30 h and then at 25° C., 500 rpm, 0.05 vvm of air, open pH, for 24 hours. In both cases, a mycelium containing many large bulges full of inclusions (including peroxysomes) should be obtained.

125 l of 1.5× malt medium are then prepared in a 300 l fermentor:

| | |
|---|---|
| Malt extract: | 6.188 kg |
| Yeast extract: | 0.938 kg |
| H₂O qs: | 125 l |

The medium is sterilized for 40 minutes at 121° C. The fermentor and its parts are sterile and pressurized. The temperature is stable and regulated at 27° C. The pressure is flushed and an air flow rate of 3.5 l/l/h, i.e. approximately 0.6 m³/h, is maintained. The base (10 N NaOH), the acid (85% H₃PO₄), the antifoam and the 6 l fermentor which serves as inoculum are sterilely brought together. The agitation speed is adjusted to 325 rpm, the antifoam is initiated, and then the inoculum (5 l) is inoculated, open pH. The agitation speed is maintained at 325 rpm and the aeration is increased to 2.2 m³/h (0.3 vvm). Growth is allowed to continue for 24 hours, so as to have approximately 10 g/l of mycelium on a dry weight basis: this mycelium should be a "compot" mycelium and should consist of filaments comprising numerous bulges and swellings, without spores.

EXAMPLE 2

Steps c and d: Conversion of Lauric Acid by the *Mortierella* Sp. Strains

Once the amount and the quality of mycelium have been attained, the substrate (lauric acid) is dispensed in mygliol. Glucose is continuously dispensed, in parallel, at the flow rate of 0.36 g/l/h for 55 h. The pH is regulated at 7 throughout the duration of the fermentation, with 5 N NaOH. The speed is increased to 900 rpm and aeration is carried out at the flow rate of 1 vvm, i.e. 12 m³/h. The conversion is pursued for 55 hours. A yield of 12 g/l of (S)-gamma-dodecalactone is obtained. By way of comparison, gamma-dodecalactones are prepared according to the teaching of patent U.S. Pat. No. 5,457,036 (Han), using the *Mortierella* strains described in U.S. Pat. No. 5,457,036.

When the Han process is used, the yields obtained are of the order of from 4 to 6.5 g/l; in comparison, when the process of the invention is employed, using a "compot" mycelium bulging with inclusions, the yield is of the order of from 12 to 15 g/l.

EXAMPLE 3

Steps c and d: Conversion of Caprylic Acid by the *Mortierella* Sp. Strains

Once the amount and the quality of mycelium have been attained, the substrate is dispensed at the flow rate of 0.75 g/l/h for 6 h. Glucose is continuously dispensed, in parallel, at the flow rate of 0.36 g/l/h. The pH is regulated at 6.5 throughout the duration of the fermentation, with 5 N NaOH. The speed is increased to 600 rpm and aeration is carried out at the flow rate of 3.5 l/min. The conversion is pursued for 48 to 74 hours. A yield of from 15 to 25, in general approximately 9 g/l, of (S)-gamma-octalactone is obtained.

By way of comparison, gamma-octalactones are prepared according to the teaching of patent EP 519481 (Farbood), using the *Mortierella* strains described in patent EP 519481; the optical rotation of the product obtained according to the Farbood process is −28°, which signifies that this product is a mixture of (R) and (S), with (S) being very slightly predominant; the optical rotation of the product attained according to the process of the invention is −42°, which shows a selectivity of the reaction for the production of (S)-gamma-lactone.

When the Farbood process is used, the yields obtained are of the order of from 7.5 to 10 g/l; in comparison, when the process of the invention is employed using a "compot" mycelium bulging with inclusions, the yield is of the order of from 15 to 25 g/l.

EXAMPLE 4

Steps c and d: Conversion of Caproic Acid by the *Mortierella* Sp. Strains

Once the amount and the quality of mycelium have been attained, the substrate is dispensed at the flow rate of 0.3 g/l/h for 6 h. Glucose is continuously dispensed, in parallel, at the flow rate of 0.36 g/l/h. The pH is regulated at 6.5 throughout the duration of the fermentation, with 5 N NaOH. The speed is increased to 600 rpm and aeration is carried out at the flow rate of 3.5 l/min. The conversion is pursued for 48 to 74 hours. A yield of 6 g/l of (S)-gamma-hexylactone is obtained.

EXAMPLE 5

Steps c and d: Conversion of Undecylenic Acid by the *Mortierella* Sp. Strains

Once the amount and the quality of mycelium have been attained, the undecylenic acid is dispensed at the flow rate of 0.3 g/l/h for 6 h and then at the flow rate of 0.53 g/l/h for 72 h: i.e. a total of 40 g/l. This undecylenic acid is dispensed as a mixture with hydrogenated sunflower oil (¼ acid-¾ oil); this oil is therefore dispensed at the flow rates of 0.9 g/l/h, then 1.53 g/l/h. Glucose is continuously distributed, in parallel, at the flow rate of 0.36 g/l/h for 72 h. The pH is regulated at 7.5 throughout the duration of the fermentation, with 5 N NaOH. The speed is increased to 505 rpm and aeration is carried out at the flow rate of 1 vvm, i.e. 12 m³/h. The conversion is pursued for 72 hours.

A production of 6.5 g/l of gamma-undecenolactone, the stereoisomerism of which is (S), is obtained.

EXAMPLE 6

Steps c and d: Conversion of Undecanoic Acid by the *Mortierella* Sp. Strains

Once the amount and the quality of mycelium have been attained, the undecanoic acid is distributed at the flow rate of 0.3 g/l/h for 6 h, then at the flow rate of 0.53 g/l/h for 3.5 h, then 0.75 g/l/h for 3.5 h, then 1 g/l/h for 48 h. This undecanoic acid is dispensed as a mixture with hydrogenated sunflower oil (¼ acid-¾ oil). Glucose is continuously distributed, in parallel, at the flow rate of 0.36 g/l/h for 24 h. The pH is regulated at 7.5 throughout the duration of the fermentation, with 5 N NaOH. The speed is increased to 505 rpm and aeration is carried out at the flow rate of 1 vvm, i.e. 12 m³/h. The conversion is pursued for 48 hours.

A production of 19 g/l of gamma-undecalactone, the stereoisomerism of which is (S), is obtained.

EXAMPLE 7

Steps c and d: Conversion of Undecylenic Acid by the *Aspergillus* Sp. Strains

Once the amount and the quality of mycelium have been attained, the undecylenic acid is dispensed at the flow rate of 0.3 g/l/h for 6 h, then 0.53 g/l/h for 72 h: i.e. a total of 40 g/l. This undecylenic acid is dispensed as a mixture with hydrogenated sunflower oil (¼ acid-¾ oil). Glucose is continuously dispensed, in parallel, at the flow rate of 0.36 g/l/h for 72 h. The pH is regulated at 6.5 throughout the duration of the fermentation, with 5 N NaOH. Aeration is carried out at the flow rate of 0.5 vvm, i.e. 6 m³/h. The conversion is pursued for 80 hours. A production of 0.5 g/l of gamma-undecenolactone, the stereoisomerism of which is (R), is obtained.

EXAMPLE 8

Steps c and d: Conversion of Caproic Acid by the *Aspergillus* Sp. Strains

Once the amount and the quality of mycelium have been attained, the caproic acid is dispensed at the flow rate of 1.64 g/l/h for 24 h, then 2 g/l/h for 72 h: i.e. a total of 183 g/l. This caproic acid is dispensed as a mixture with hydrogenated sunflower oil (½ acid-½ oil). Glucose is continuously distributed, in parallel, at the flow rate of 0.36 g/l/h. The pH is regulated at 6.5 throughout the duration of the fermentation, with 5 N NaOH. Aeration is carried out at the flow rate of 0.5 vvm, i.e. 6 m³/h. After 72 h to 96 h, a production of 15 g/l of gamma-hexylactone, the stereoisomerism of which is (R), is obtained.

EXAMPLE 9

Step e: Extraction—Purification

Acidification at pH 1.5 is carried out with 3 l of 85% phosphoric acid. Heating is carried out at more than 100° C. for 30 minutes in order for the lactone to be essentially in its cyclized form and not in its open hydroxy acid form. The lactone is quantitatively determined, extraction solvent is added (preferably cyclohexane), and the mixture is stirred at ambient temperature for 1 hour. Centrifugation is carried out and the organic phase is recovered. The lactone is quantitatively determined. The solvent is concentrated and an oily "crude" is thus obtained. Vacuum distillation is carried out. The "deresined" lactone and an exhausted oil are obtained. Purification is subsequently carried out by fractionating the lactone under vacuum. A product that is >99% pure is obtained, which product is either gamma-undecenolactone (>99% S) if a strain of *Mortierella* sp. was used, or gamma-undecenolactone (>99% R) if a strain of *Aspergillus* sp. was used.

The gamma-undecenolactone, (R) or (S), or a mixture of (R) and (S), and also the gamma-undecalactone, (R) or (S), or a mixture of (R) and (S), can be used in perfuming compositions in order to contribute to providing exotic, floral or fruity notes, which has resulted in the applicant registering the trade mark "Tropicalone®" given to the gamma-undecenolactone. According to the applications, the (S) enantiomer or the (R) enantiomer, or else a mixture of the 2 enantiomers in proportions determined by a person skilled in the art, will be used.

What is claimed is:

1. A process for the stereoselective preparation of a gamma-lactone of formula (I)

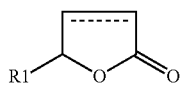 (I)

wherein the lactone ring can be unsaturated between carbon 2 and carbon 3, or is saturated, and R1 is a $C_{2-16}$ alkenyl, $C_{2-16}$ alkynyl or $C_{1-16}$ alkyl, comprising the following steps:
a) culturing a microorganism from the genus *Aspergillus* or the genus *Mortierella* in an appropriate culture medium free of peptone to produce a cell culture having a mycelium composed of compartmentalized filaments with no conidiospores and exhibiting bulging structures, said culturing being optionally preceded by a step consisting of preculturing the microorganism,
b) adding a substrate selected from the group consisting of fatty acids having at least five carbon atoms and methyl or ethyl esters thereof to said culture,
c) hydroxylating the substrate at carbon 4 of the fatty acid moiety and converting the hydroxylated substrate into gamma-lactone of formula (I), wherein said hydroxylating and converting is accomplished by the microorganism, and
d) recovering the gamma-lactone produced.

2. The stereoselective process as claimed in claim 1 wherein the microorganism is chosen from a strain of the genus *Aspergillus* and said strain produces an (R)-gamma-lactone.

3. The stereoselective process for the preparation of (R)-gamma-lactone as claimed in claim 2, wherein the microorganism is a strain of *Aspergillus oryzae*.

4. The stereoselective process as claimed in claim 3, wherein the strain of *Aspergillus oryzae* is selected from the group consisting of: DSMZ 1861, DSMZ 1864, DSMZ 1147, DSMZ 63303, CBS 570.65, CBS 819.72, and CBS 110.27.

5. The stereoselective process as claimed in claim 1, wherein the microorganism is chosen from a strain of the genus *Mortierella* and said strain produces an (S)-gamma-lactone.

6. The stereoselective process for the preparation of (S)-gamma-lactone as claimed in claim 5, wherein the wherein the microorganism is strain of *Mortierella isabellina*.

7. The stereoselective process as claimed in claim 6, wherein the strain of *Mortierella isabellina* is selected from the group consisting of: DSMZ 1414, CBS 100559, CBS 221.29, CBS 194.28, CBS 208.32, CBS 224.35, CBS 560.63, CBS 167.80, CBS 493.83, CBS 309.93, CBS 250.95 and CBS 109075.

8. The process as claimed in claim 1, wherein said substrate is chosen from linear fatty acids containing from 5 to 20 carbons, and the methyl or ethyl esters of said fatty acids.

9. The process as claimed in claim 8, wherein the substrate is selected from the group consisting of valeric acid, caproic acid, enanthic acid, caprylic acid, pelargonic acid, decanoic acid, undecanoic acid, undecylenic acid, lauric acid, myristic acid, palmitic acid, palmitoleic acid, stearic acid, oleic acid, linoleic acid, linolenic acid, eicosanoic acid, ethyl or methyl esters thereof, and a mixture thereof.

10. The process as claimed in claim 1, wherein the substrate is added in step b) as a mixture with glucose and at least one production auxiliary product selected from the group consisting of oils, mygliol and a mixture thereof.

11. The process as claimed in claim 10, wherein said production auxiliary product is sunflower oil.

12. The process as claimed in claim 1, wherein step d) is carried out by extracting the gamma-lactone by hydrodistillation, optionally followed by esterification of the substrate which has not reacted and the elimination of said esterified substrate.

13. The process as claimed in claim 1, wherein step d) is carried out by extracting the gamma-lactone obtained at the end of step c) with a solvent.

* * * * *